(12) United States Patent
Whitcombe et al.

(10) Patent No.: US 7,001,721 B1
(45) Date of Patent: Feb. 21, 2006

(54) NUCLEIC ACID SEQUENCE IDENTIFICATION

(75) Inventors: David Mark Whitcombe, Northwich (GB); Duncan Graham, Glasgow (GB); William Ewen Smith, Glasgow (GB)

(73) Assignee: University of Strathclyde, Glasgow (GB)

( * ) Notice: Subject to any disclaimer, the term of this patent is extended or adjusted under 35 U.S.C. 154(b) by 0 days.

(21) Appl. No.: 09/700,732

(22) PCT Filed: May 20, 1999

(86) PCT No.: PCT/GB99/01597

§ 371 (c)(1),
(2), (4) Date: Mar. 19, 2001

(87) PCT Pub. No.: WO99/60157

PCT Pub. Date: Nov. 25, 1999

(30) Foreign Application Priority Data

May 20, 1998 (GB) ............................................. 9810865

(51) Int. Cl.
| | |
|---|---|
| *C12Q 1/68* | (2006.01) |
| *C12N 15/00* | (2006.01) |
| *C12N 15/63* | (2006.01) |
| *C12N 1/20* | (2006.01) |
| *C07H 21/04* | (2006.01) |

(52) U.S. Cl. ..................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1

(58) Field of Classification Search ...................... 435/6, 435/91.1, 91.2, 5; 536/24.3; 935/6, 77, 78; 436/518, 164, 173, 525, 801, 805
See application file for complete search history.

(56) References Cited

U.S. PATENT DOCUMENTS

| 5,266,498 | A | | 11/1993 | Tarcha |
| 5,306,403 | A | | 4/1994 | Vo-Dinh |
| 5,721,102 | A | | 2/1998 | Vo-Dinh |
| 6,127,120 | A | * | 10/2000 | Graham ........................ 435/6 |

FOREIGN PATENT DOCUMENTS

| EP | 0 667 398 A2 | 8/1995 |
| EP | 0 838 528 A1 | 4/1998 |
| WO | WO 96/41181 | 12/1996 |
| WO | WO 97/05280 | 2/1997 |

OTHER PUBLICATIONS

Kneipp, K. et al., "Surface Enhanced Raman Scattering (SERS) of nucleic Acids Adsorbed on Colloidal Silver Particles"; Journal of Molecular Structure, 145: 173–179 (1986) [Abstract].

Munro, C.H. et al., "Qualitative and Semi–quantitative Trace Analysis of Acidic Monoazo Dyes by Surface Enhanced Resonance Raman Scattering"; Analyst, 120: 993–1003 (1995).
Helmenstine, A. et al., "Measurement of DNA Adducts Using Surface–Enhanced Raman Spectroscopy"; Journal of Toxicology and Environmental Health, 40: 195–202 (1993).
Mirkin, C.A. et al., "A DNA–based method for rationally assembling nanoparticles Into macroscopic materials"; Nature, 382: 607–609 (1996).
Storhoff, J.J. et al., "One Pot Colormetric Differentiation of Polynucleotides with Single Base Imperfections Using Gold Nanoparticle Probes"; J. Am. Chem. Soc., 120: 1959–1964 (1998) [Abstract].
Bethell, D. et al., "Nanotechnology and nucleotides"; Nature, 382: 581 (1996).
Alivisatos, A.P. et al., "Organization of 'nanocrystal molecules' using DNA"; Nature, 382: 609–611 (1996).
Munro, C.H. et al., "Characterization of the Surface of a Citrate–Reduced Colloid Optimized for Use as a Substrate for Surface–Enhanced Resonance Raman Scattering"; Langmuir, 11: 3712–3720 (1995).
Bertoluzza, A. et al., "Raman and Infrared Spectra of Spermidine and Spermine and their Hydrochlorides and Phosphates as a Basis for the Study of the Interactions Between Polyamines and Nucleic Acids"; Journal of Raman Spectroscopy, 14(6): 386–394 (1983).
Cotton, T.M., "Application of Surface–Enhanced Raman Spectroscopy to Biological Systems"; Journal of Raman Spectrocopy, 22: 729–742 (1991).
Egholm, M., "Spectrometry senses more than a small difference"; Nature Biotechnology, 15: 1346 (1997).
Graham, D. et al., "Selective Detection of Deoxyribonucleic Acid at Ultralow Concentrations by SERRS"; Analytical Chemistry, 69(22): 4703–4707 (1997).
Rodger, C. et al., "Surface–enhanced resonance–Raman scattering: an informative probe of surfaces"; J. Chem. Soc. Dalton Trans., 791–799 (1996).

* cited by examiner

*Primary Examiner*—Jeffrey Fredman
*Assistant Examiner*—Arun Chakrabarti
(74) *Attorney, Agent, or Firm*—Dann, Dorfman, Herr & Skillman, P.C.

(57) ABSTRACT

Disclosed are methods for determining the presence or absence of a target nucleic acid (e.g. DNA) sequence in a sample nucleic acid, the method comprising: (a) exposing the sample to a detection agent comprising a colloid metal surface associated with a SER(R)S active species (SAS) such as an azo dye and with a target binding species (TBS) which may be PNA which is complementary to the target, and (b) observing the sample agent mixture using SER(R)S to detect any surface enhancement of the label wherein the binding of the TBS to the target sequence causes surface enhancement SAS. The detection agent may be exposed to the sample in step (a) as two or more separate components and will generally comprise a first agent and a second agent each having a different TBS, each TBS being capable of binding to the target sequence, and wherein the binding of the first and second TBS to the target sequence brings a metal surface associated with each TBS into proximity thereby causing surface enhancement of an SAS associated with one or both of the metal surfaces.

17 Claims, 9 Drawing Sheets

A1

A2

A3

A4

A7

A8

Figure 1:
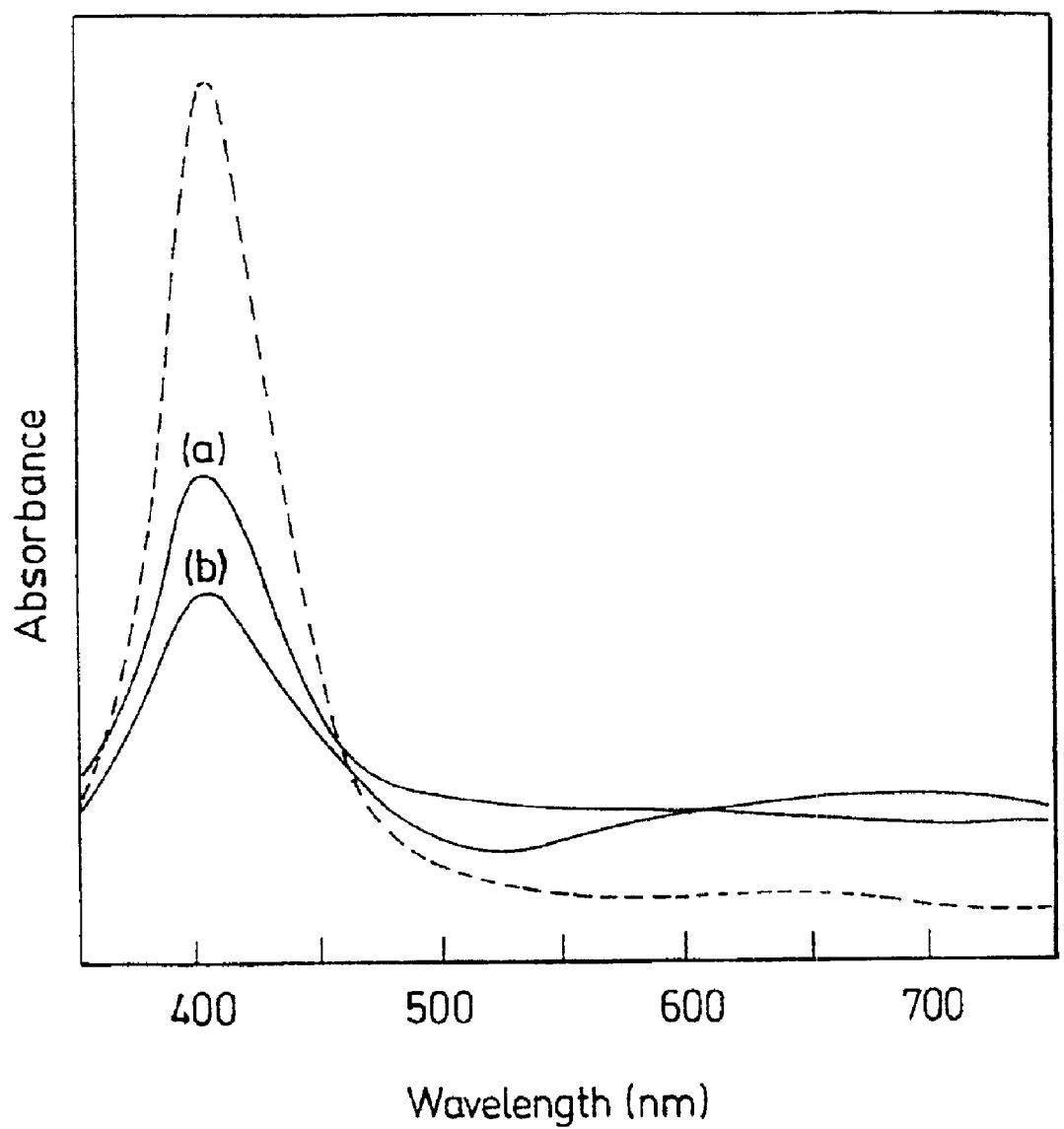

Where $R_{10}$ = $(CH_2)_n$ – COOH
$(CH_2)_n$ – $PPh_2$
$(CH_2)_n$ – SH
$(CH_2)_n$ – $NH_2$
$(CH_2)_n$ – OH
H
n = 0–4

A9

A10

A5  A6

Where $R_1 - R_6$ =
- phenyl, naphthyl, pyridyl etc
- analyte
- CH=CHR
- 
- C=NR
- C=N⁺R
  |
  O⁻
- C(H)O
- C(R)O
- C(NHR)O
- CH₂NHR
- CH₂OR
- CH₂halogen
- N₃
- NO
- NO₂

- NHCONHR
- NHCSNHR
- NHCOR
- NHR
- OH
- OR
- SiR₃
- SH
- SR
- SSR
- SeR
- SnR₃
- PbR₃
- where R = H or any alkyl, aryl group W,X,Y,Z = C,O,S or N
n,m = any integer >1

A11

A12

A13

Where X=N or C $R_{11}$ = –Ph–N=N–$R_9$
or –$CH_2$–Ph–N=N–$R_9$

(ii) Genomic Material

NUCLEIC ACID SEQUENCE IDENTIFICATION

TECHNICAL FIELD

The present invention relates to methods and materials for detecting or identifying particular nucleic acid sequences in a sample using surface enhanced resonance Raman scattering ('SERRS').

PRIOR ART

There is currently a great demand for technologies which can detect either specific sequences, or single point mutations or polymorphisms in a targeted sequence of nucleic acid from a particular source. Information derived from such methods can be used in numerous aspects of genetic investigation.

Thus the identification of particular target sequences may be used in diagnosis and detection of particular agents containing that sequence (e.g. invasive pathogens such as a viruses) or to isolate larger sequences containing the target sequence.

The detection of nucleic acid variants is used in evolutionary and population structure studies, forensics, and the analysis and diagnosis of genetic disease. Variations in DNA sequence between individuals may be used to identify or isolate genes or subsequences associated with particular traits, for instance disease traits within organisms of interest such as humans.

Some current methodologies used for detecting (scanning or scoring) nucleic acid variants are reviewed by Schafer & Hawkins (1998) Nature Biotechnology 16: 33–39.

These methods include single strand conformation polymorphism analysis (SSCP), heteroduplex analysis (HA), denaturing gradient gel electrophoresis (DGGE), duplex cleavage (e.g. using RNase, chemistry, or endonucleases). Scoring methods include minisequencing, nuclease assays or standard Sanger sequencing.

Most of these methods rely on the specific binding of probe or primer to the targeted sequence, followed by the detection of the binding event (e.g. by stability, mobility, or the presence of a label). Owing to the sensitivity of the detection methods, amplification of the sample (e.g. by PCR) is usually required before hybridisation. This is undesirable because of the possibility that errors may occur during the amplification process, leading to false positive or negative results.

A particularly sensitive method for identifying labelled nucleic acids is disclosed by Graham et al (1997) Anal Chem 69: 4703–4707. This relies on the use of surface enhanced resonance Raman scattering (SERRS), which is in turn a development of surface enhanced Raman scattering (SERS).

Briefly, a Raman spectrum arises because light incident on an analyte is scattered due to excitation of electrons in the analyte. "Raman" scattering occurs when an excited electron returns to an energy level other than that from which it came—this results in a change in wavelength of the scattered light and gives rise to a series of spectral lines at both higher and lower frequencies than that of the incident light. The scattered light can be detected orthogonally to the incident beam.

Normal Raman lines are relatively weak and Raman spectroscopy is therefore too insensitive, relative to other available detection methods, to be of use in chemical analysis. Raman spectroscopy is also unsuccessful for fluorescent materials, for which the broad fluorescence emission bands (also detected orthogonally to the incident light) tend to swamp the weaker Raman emissions.

However, a modified form of Raman spectroscopy, based on SERS, has proved to be more sensitive and hence of more general use. The analyte whose spectrum is being recorded is closely associated with a roughened metal surface. This leads to a large increase in detection sensitivity, the effect being more marked the closer the analyte sits to the "active" surface (the optimum position is in the first molecular layer around the surface, i.e., within about 2 nm of the surface).

The theory of this surface enhancement is not yet fully understood, but it is thought that the higher valence electrons of the analyte associate with pools of electrons (known as "plasmons") in pits on the metal surface. When incident light excites the analyte electrons, the effect is transferred to the plasmons, which are much larger than the electron cloud surrounding the analyte, and this acts to enhance the output signal.

A further increase in sensitivity can be obtained by operating at the resonance frequency of the analyte (in this case usually a dye attached to the target of interest). Use of a coherent light source, tuned to the absorbance maximum of the dye, gives rise to a $10^3$–$10^5$-fold increase in sensitivity. This is termed "resonance Raman scattering" spectroscopy. In certain embodiments the laser excitation may be set to the maximum of the plasmon resonance. In certain cases the plasmon resonance and dye maxima may coincide.

When the surface enhancement effect and the resonance effect are combined, to give SERRS, the resultant increase in sensitivity and robustness is more than additive. Moreover, the sensitivity does not seem to depend so critically on the angle of orientation of the analyte to the surface, as is the case with SERS alone. A SERRS signal can be more easily discriminated from contamination and background and tends to be less variable with local conditions (e.g., ionic strength or pH when an analysis is carried out in solution). Fluorescence is also quenched, giving cleaner Raman spectra and allowing fluorescent dyes to be used as detectable analytes. Generally, the signal enhancement means that a much larger range of analytes may be usefully detected than using normal Raman spectroscopy. Furthermore, the enhancement means that a less powerful light source is required to excite the analyte molecules.

With SERRS, detection limits down to one molecule have been achieved for compounds which absorb light in the visible wavelength region or the electromagnetic spectrum (see Emory & Nie (1997) "Near-Field Surface-Enhanced Raman Spectroscopy on Single Silver Nanoparticles", Anal. Chem. 69: 2631–2635). This technique is therefore more sensitive than fluorescence (see eg, C Rodger et al, *J. Chem. Soc. Dalton Trans.* (1996), pp791–799) and furthermore, the SERRS spectra obtained contain molecular information which permit compound identification and discrimination.

WO 97/05280 (University of Strathclyde) discloses practical demonstrations of the use of SE(R)RS in nucleic acid detection and sequencing. The methods disclosed therein are based generally around the use of a labelled targetting species which binds to a target species if present to form a complex. The complex is then associated with a SER(R)S surface, and is detected using suitable equipment.

U.S. Pat. No. 5,721,102 (Vo Dinh et al) describes a labelled SER gene probe which is used to hybridise to (and label) complementary sequences. Non-hybridised material is separated from the hybridised material, and the hybridised material is analysed.

It will be clear from the above that novel formats for detecting or identifying particular nucleic acid sequences in a sample, particular those which have one or more advantages over those in current use, would provide a contribution to the art.

DISCLOSURE OF THE INVENTION

The present inventors have devised a novel SERS/SERRS based method for detecting or identifying a particular nucleic acid sequence in a sample. Not only does it not require amplification of the sample prior to detection, but in preferred formats the method can be carried out using simple, one pot, mixing procedures to provide a rapid, highly-sensitive, detection of target sequences without any requirement to separate unbound labelled targeting agent from labelled target complexes. This is achieved by making the functionality of the SER(R)S surface dependent on the presence of the target sample. Thus, unlike in certain existing techniques based on labelled probes, unbound labelled target will not generate a false result if present during detection.

The present invention may be used in either a SERS or SERRS format, and the abbreviation SER(R)S is used hereinafter to demonstrate this. Generally speaking, owing to its sensitivity advantages, SERRS will be preferred.

In known nucleic acid detection formats, such as those described in WO 97/05280 (University of Strathclyde), metal colloid which has been carefully aggregated in a controlled manner is added to labelled target complex prior to detection. In the present invention, the aggregation of colloidal SER(R)S surface is actually dependent on the presence of target sequence, with the attendant advantages described above.

Thus in a first aspect of the present invention there is disclosed a method for determining the presence or absence of a target nucleic acid sequence in a sample nucleic acid, the method comprising:
(a) exposing the sample to a detection agent comprising a metal surface associated with a SER(R)S active species (SAS) and with a target binding species (TBS),
(b) observing the sample/agent mixture to detect any surface enhancement of the label.

The method is characterised in that it is the binding of the TBS to the target sequence which itself causes surface enhancement of the SAS.

Equally the method differs from those in the art in that the metal surface, in the form in which it is present in the added agent, is not itself capable of surface enhancement. Thus any unbound detection agent present in the system following exposure of the sample to the agent need not be removed prior to the observation step. Thus, given that the detection agent will generally be present at great excess over the target material, unbound agent will be present in the system during detection, but owing to the nature of the method, will not interfere with the result. The method is therefore a true "one pot" detection system.

The result of the observation is correlated with the presence or absence of the target sequence, optionally by comparison with reference data.

The method is particularly susceptible to giving rapid information about whether a known, or at least predetermined, target sequence occurs in a nucleic acid source.

The detection agent may be exposed to the sample in a number of separate steps, or as a number of separate components, provided that ultimately all the required components are present in the system.

In a preferred embodiment of the method, the detection agent comprises a first agent and a second agent each having a different TBS, each TBS being capable of binding to the target sequence, and wherein the binding of the first and second TBS to the target sequence brings a metal surface associated with each TBS into proximity thereby causing surface enhancement of an SAS associated with one or both of the metal surfaces.

Generally the first and second TBS will bind adjacent each other in order to bring their respective metal surfaces into contact or near contact.

Oligonucleotides have been used previously to assemble metal clusters (gold colloid) into superlattices (see Bethell and Schiffrin (1996) Nature Vol 382: pg 581, plus also Mirkin et al and Alivisatos et al on pgs 607–609 and 609–611 of the same issue). However these publications were concerned generally with the production of macroscopic materials from nanoparticles (so called 'nanotechnology'), the nucleic acid being used to assist in the assembly process. Assembly was detected by calorimetric differentiation. A further paper (Storhoff et al, 1998 "One pot colorimetric differentiation of polynucleotides with single base imperfections using gold nanoparticle probes" J Am Chem Soc 120: 1959–1964) also used calorimetric analysis for detecting aligned gold nanoparticle probes. However no vibrational spectroscopy was carried out on the assembled structures. No suggestion of the technique's application in the field of raman spectroscopy was made.

The present, SER(R)S-based, invention will now be explained in more detail with reference to some of the preferred embodiments.

The "sample nucleic acid" can be any nucleic acid, including DNA (from any source e.g. genomic, cDNA, synthetic etc.), RNA (e.g. mRNA, tRNA, rRNA, synthetic etc.) or derivatives of these. Generally it will be at least 16 nucleotides in length, more preferably at least 24, 30, 40, 50, 100 or 200 nucleotides in length. The sample can represent all or only some of the nucleic acid present in a given source. The sample may be prepared prior to testing in order to make the sample nucleic acid therein more available for the testing process. For instance the sample nucleic acid may be fully or partially purified and/or fragments may be produced and separated. As an alternative to, or in addition to, using the nucleic acid in the sample directly, copies may be prepared and used (e.g. using PCR). The term "sample nucleic acid" covers all of these possibilities.

Generally the sample nucleic acid will be prepared as single strand nucleic acid prior to the sequence detection.

If desired the sample may be blotted, tethered or otherwise immobilised on a solid phase, optionally in the form of an array (e.g. a so called nucleic acid chip—see e.g. Marshall & Hodgson (1998) Nature Biotechnology 16: 27–31).

The "target" sequence itself may be any sequence of any length within the sample which it is desired to investigate. Thus it may be any sequence found in a genome, or subgenomic nucleic acid, chromosome, extrachromasomal vector, or gene, or motif, or non-coding sequence, or a sequence tagged site, or expressed sequence tag. The sequence may be derived from any source e.g. published material on a database.

The sequence may be unique within a given genome, or may have multiple occurrences within it (the methods of the present invention may be used to determine its frequency of occurrence). Likewise the sequence may be unique to a particular individual, or population, or species, genus, family etc. or be present within more than one of these groupings. The length of the target sequence may be selected on the basis of its statistical likelihood of chance occurrence within a given size of genome. For instance it has been suggested that a sequence of up to 16 bases in yeast, and a few more in humans (e.g. 17–24), may be sufficient to indicate a unique sequence in these organisms.

Particularly envisaged is the detection of nucleic acid 'variants'. These may include single nucleotide variants (mutations or polymorphisms) or variable number tandem repeats, or other satellite or microsatellite repeats. Thus the target sequence in these cases may be characterised by only a single base, or numbers of pairs of bases, within a given longer sequence.

As set out in more detail below, it may be desirable to probe several target sequences simultaneously using appropriate, distinctive agents.

The "exposure" of the sample to the agent can take any form which brings the two into sufficient contact to allow binding of the agent to the target sequence of the sample. Generally this will be mixing of solutions of these components.

The "detection agent" has a number of important attributes, although it is stressed that it may comprise a number of discrete parts which are added simultaneously or even sequentially.

The metal surface

The agent comprises a metal surface. As discussed above, this surface is initially present in a form which minimises surface enhancement under the conditions selected for the SER(R)S observation step, but becomes SER(R)S active when the TBS binds to the target sequence.

Thus the methods of the present invention exploit the fact that the properties of the surface to which a Raman active label is associated, have a profound effect on the degree of surface enhancement which can be achieved. Using unaggregated silver colloid, for example, surface enhancement is at a minimum and results in unrecognisable, indistinct signals at wavelengths commonly used in SER(R)S detection formats. By contrast, once aggregated, the SERRS signals obtained are strong, definable and characteristic of a specific analyte. This effect is discussed generally in Munro et al (1995) Langmuir 11: 3712–3720. In essence these authors showed that monodisperse colloidal silver particles (of around 27 nm in size) have a maximum absorption wavelength of around 400 nm, which is consistent with the excitation of dipolar surface plasmons. Aggregated colloid (for instance consisting of two or more silver particles in close association) shows a clear shift in absorbance to higher wavelengths, with a much higher absorbance above 500 nm than was exhibited by the monodisperse particles. The visible absorbance spectra for aggregated and unaggregated particles is shown in FIG. 1. It is this region (e.g. 500 to 600 nm) which is much more useful for carrying out SER(R)S. SER(R)S surfaces are also discussed by Rodger et al (1996) J Chem Soc Dalton Trans, pg 791–799.

The surface may be provided by a naked metal or may comprise a full or partial coating. It may include, for instance, a metal oxide layer, or an organic coating such as citrate, or borohydride.

Generally the metal surface will be provided by unaggregated colloidal metal particles. For instance silver, gold or copper particles. Processes for preparing such unaggregated colloids are now well known in the art. They involve, for instance, the reduction of a metal salt (eg, silver nitrate) with a reducing agent such as citrate, to form a stable microcrystalline suspension (see P C Lee & D Meisel, *J. Phys. Chem.* (1982), 86, p3391).

The colloid particles are preferably monodisperse in nature. Preferably they will be about 20–35 nm in diameter, though this will depend on the type of metal.

Preferably, the metal surface is provided by discrete silver colloid particles, which are preferably substantially hexagonal in shape and of about 35 nm maximum diameter.

In embodiments employing metal colloid, the binding of the TBS to the target sequence causes individual colloidal metal particles to be brought into proximity, thereby aggregating them, or at least mimicing the effects of aggregation, such as to cause surface enhancement of an SAS which is associated with the "aggregated" particles i.e. causing an enhancement of signal at the selected wavelength.

As used hereinafter, unless context demands otherwise, the terms "aggregation" or "aggregates" describe this effect.
TBS The TBS of the agent will generally be based on a nucleic acid, or modified nucleic acid, or nucleic acid analog, which is complementary to all or part of the target sequence.

Under certain circumstances (when the TBS is not being synthesised to order for instance) it may not be necessary to know its sequence. For instance nucleic acid may be taken from a (known) source, cleaved, and the cleaved portions can be used to prepare the detection agent of the present invention. Thus the target (original source) is predetermined, even if the sequence is not established.

By "complementary" is capable of specific base pairing with the target sequence whereby A is the complement of T (and U); G is the complement of C. Generally complementary nucleic acids run anti-parallel i.e. one runs 5' to 3', while the other 3' to 5'. Where modified nucleic acid, or nucleic acid analog is used, the base pairing is between corresponding modified or analog bases and the complementary target sequence as appropriate.

It will be understood by those skilled in the art that, for a given target sequence and target binding species, 100% complementarity of the full length of the sequences may not be required to ensure hybridisation between the two (see e.g. *Molecular Cloning: a Laboratory Manual:* 2nd edition, Sambrook et al, 1989, Cold Spring Harbor Laboratory Press, or later editions of that work, for a discussion of appropriate conditions to achieve nucleic acid hybridisation). Thus sequences which are only substantially complementary may also hybridise under appropriate conditions, thereby causing the aggregative effect discussed above and hence surface enhancement of the SAS.

It is known that normally nucleic acid hybridisation conditions require the presence of salt to prevent the repulsion of the negative phosphate backbones. However if salt is added to the colloidal suspension then aggregation may occur producing a false result. This may be avoided by modification of the nucleic acid and/or colloid, or use of a nucleic acid analog.

For instance it is known that DNA forms which are neutral, or at least zwitterionic, do not require high salt concentrations for hybridisation to occur. One possible example of this is propargyl amino modified base as described by Cruickshank & Stockwell (1988) Tetrahedron Letters 29: 5221–5224, and later in Graham et al (1997) Anal Chem 69: 4703–4707. This particular modification is also believed to promote greater specificity of base pairing (see Wagner et al (1993) Science 260: 1510–1513).

In another embodiment peptide nucleic acid (PNA) is used for the probes which assemble the colloid. PNAs do not require salt for hybridisation due to their neutral backbone and bind with a greater specificity of base pairing and will not tolerate mismatches. Also, the subsequent duplex formed displays much greater stability than a DNA/DNA duplex. These properties mean a strand of PNA shorter than the corresponding DNA probe can be used to much greater effect. The use of PNA in the context of MALDI-TOF mass spectrometry for sequence identification is briefly reviewed by Egholm (1997) Nature Biotechnology 15: pg 1346. In that process an amplification step is advocated. PNA in chip technology is discussed by Marshall & Hodgson (1998) Nature Biotechnology 16: pg 27–31.

As discussed above, generally two different (non-complementary to each other) TBS will be used which are capable of binding adjacent, or at least closely, to each other in the target sequence (but will not be brought together in the absence of the target sequence).

Preferably, when the first and second TBS are bound to the target sequence they are adjacent, or separated by 1, 2, 3, 4, 5, fewer than 10, 20 or 30 bases, in order to effect aggregation.

It may be desirable to have several TBS per agent (e.g. spaced around a metal colloid particle) for instance more than 1, 2, 3, 4, 5, 10, or 20 per agent. Agents of this sort may be cross-linked in the presence of the target sequence. This can generate larger aggregates of metal surface, with a corresponding shift in the plasmon resonance wavelength.

Association of TBS with metal surface

The interaction between the SSG and the metal surface will typically be by chemi-sorption of the complex onto the surface, or by chemical bonding of the complex with a coating on the surface.

This is preferably achieved by means so called "surface seeking groups" (SSGs). These bind extremely tightly to the metal surface, and are discussed in detail in WO 97/05280 (University of Strathclyde).

SSGs will generally be either complexing or chelating in nature, or will comprise bridging ligands or polymer forming groups.

Naturally the choice of the SSG will depend on the nature of the surface (e.g. its charge and the presence or absence of an oxide or other layer) and of any surface coatings or other species (such as citrate reducing agents) associated with it, and also on the nature of the TBS. For most useful surfaces, the functional group preferably comprises a Lewis base. Ideally, it is actively attracted to the surface in use. For gold surfaces phosphorus and sulphur containing groups may be particularly preferred, as discussed by Bethell & Schiffin cited supra.

Thus suitable groups by which the agent may be bound to the active surface include complexing groups such as nitrogen, oxygen, sulphur and phosphorous donors; chelating groups; bridging ligands and polymer forming ligands.

Figure 2:
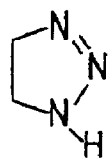
Figure 2:
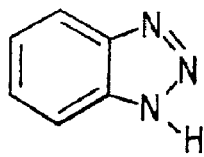
Figure 2:
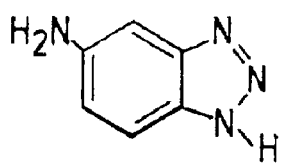
Figure 2:
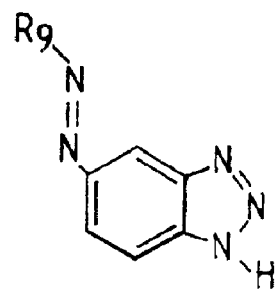
Figure 2:
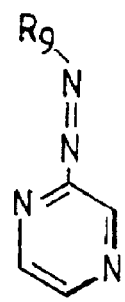
Figure 2:
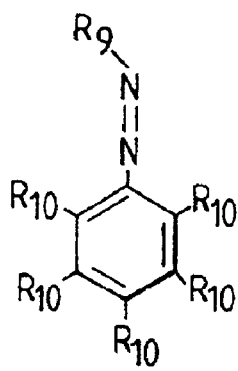
Figure 2:
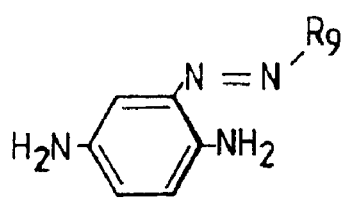
Figure 2:
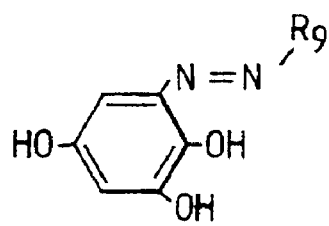
Figure 2:
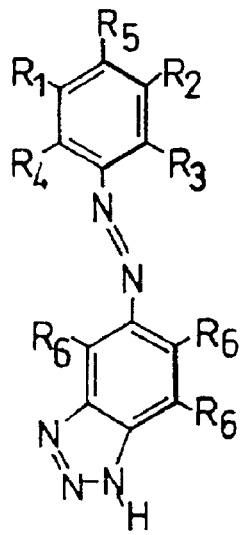
Figure 2:
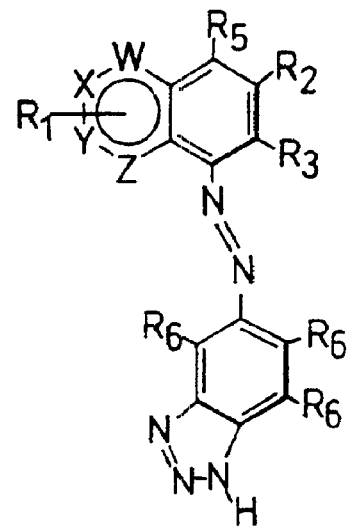
Figure 2:
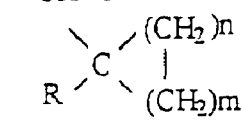
Figure 2:
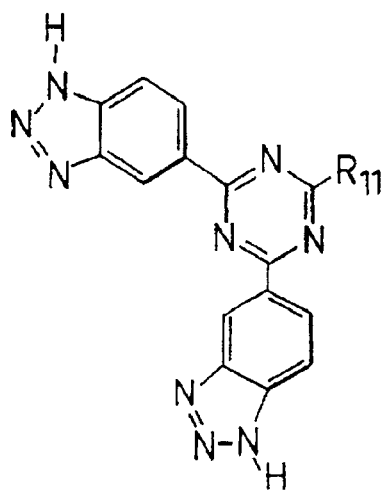
Figure 2:
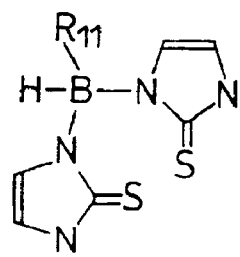
Figure 2:
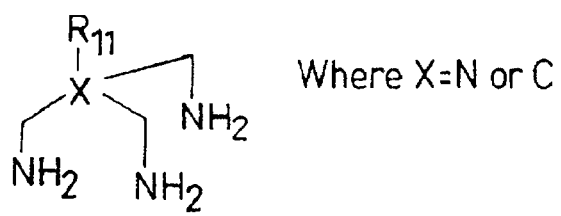

Some example SSGs are shown in FIG. 2.

The triazole group (Formula A1) is rich in nitrogen lone pairs and seems to have a particular affinity for certain metal colloids. Thus, incorporation of this group in the agent is particularly preferred, since it can increase the proximity of the label to the surface, and thereby the surface enhancement effect which occurs when the TBS binds the target sequence.

The agent preferably contains the benzotriazole group (Formula A2), particularly when the metal surface is silver- or copper-based, which has a high degree of conjugation (especially when deprotonated) and is thus particularly amenable to SE(R)RS detection which relies on label resonance.

Benzotriazole derivatives (such as that shown in Formula A3) may be readily obtained and can be coupled with existing labels (such as azo dyes) to give appropriately modified labels.

In preferred forms, the SSG is modified to be SE(R)RS active and this is used to conjugate the TBS to the metal surface. Examples of such groups include azobenzotriazoles, typically formed by combining azo substrates with benzotriazole derivatives. Examples of azobenzotriazoles include 9-(carboxyethyl)-3-hydroxy-6-oxo-6H-benzotriazole, and substituted benzoic and naphthoic acid azo derivatives coupled to benzotriazole.

An example structure for use as an agent in the present invention is the azobenzotriazole shown in Formula A4. The compound comprises an azo chromophore which increases the wavelength of the absorbance maximum of the label.

In all example structures in which it appears, $R_9$ represents the TBS (e.g. PNA), optionally via a linker. The linker may be used to affect the distance between discrete metal surfaces following succesful binding, and the rigidity with which the surfaces are held. Generally a linker of less than 5, 10 or 15 carbons in length will be preferred. Different $R_9$ groups (e.g. different linkers) can also provide the agents with molecularly specific SE(R)RS spectra.

Suitably compounds for use in the agents of the present invention labels are encompassed by the Formulae A5 and A6 wherein:

In all cases the TBS or linker will constitute one or more of $R_1$–$R_6$ groups, preferably selected from groups $R_1$–$R_5$. The following preferences therefore refer to those groups from $R_1$–$R_6$ not being the TBS/linker.

Thus the remaining $R_1$–$R_6$ can represent any appropriate groups (including hydrogen), preferably selected from those listed below the formulae.

W, X, Y and Z are defined below the formulae. A more preferred sub-set of such compounds is those in which $R_1$, $R_2$, $R_3$, $R_4$ and $R_6$ are independently selected from hydrogen, $C_1$–$C_6$ alkyl, $C_1$–$C_6$ alkoxy, 6-membered aromatic rings, halogen, —COOH, —$SO_3H$, —$PO_4$, —SH, —PO, —$NR_7$ and $R_8$; $R_5$ can be as $R_1$ or alternatively —$NH_2$ or functionalised —COOH such as —$(CH_2)_n$—COOH where n is an integer from 1 to 6; and $R_7$ and $R_8$ are independently selected from hydrogen, $C_1$–$C_6$ alkyl (linear or branched chain) and unsaturated cyclic alkyl rings.

Most preferred forms of such labels are those in which $R_1$ and $R_2$ are both hydrogen, $R_3$ and $R_4$ are independently selected from hydrogen and methoxy, $R_5$ is either —OH or -amino and $R_6$ is hydrogen.

The agents prepared in Examples 1 to 3 (see FIG. 6B and 6C), are examples of falling within these formulae.

Formula A7 provides an alternative to the benzotriazole-based agents.

Functional groups on the surface seeking portion of the agents may include charged polar groups (eg, amine, carboxyl, phosphate, thiol, hydroxyl), attracted to the surface or surface coating (e.g., to free amine groups in a polyamine coating). Examples of these are shown in Formula A8, wherein $R_9$ is as discussed above, and $R_{10}$ is independently selected from the groups listed in the figure, with no more than 3 of the $R_{10}$ groups in the formula being H. Preferably the $R_{10}$ groups in the formula, other than those which are H, are all the same, as exemplified by Formula A9 and A10.

Further alternative surface seeking groups are shown by Formulae A11, A12 and A13.

Other suitable surface seeking groups for the agent include the calixerines and the mercapto benzotriazoles.

SER(R)S active species

The agent comprises an SAS. This can be provided by a separate label in instances when the TBS is non-UV absorbing. Suitable labels are discussed in detail in WO 97/05280 (University of Strathclyde), and also in the SER(R)S literature. The label can be associated with the metal surface either as part of the TBS (optionally as part of a SSG), or quite separately from it.

In preferred embodiments of the invention, as discussed in more detail below, there will be more than one molecule of SAS per agent. Indeed the number is preferably maximised such that when an aggregated metal surface is formed as a result of a target sequence/TBS binding event, the maximum number of SAS molecules are surface enhanced by that event.

Preferably a single molecule target sequence is capable of surface enhancing more than 10, 20, 30, 40, 50, preferably more than 100, 150, or 200 SAS molecules which are associated with the metal surface of the agent binding that target sequence via the TBS.

Examples of suitable SE(R)RS-active species include fluorescein dyes, such as 5- (and 6-) carboxy-4',5'-dichloro-2',7'-dimethoxy fluorescein, 5-carboxy-2',4',5',7'-tetrachlorofluorescein and 5-carboxyfluorescein; rhodamine dyes such as 5- (and 6-) carboxy rhodamine, 6-carboxytetramethyl rhodamine and 6-carboxyrhodamine X; phthalocyanines such as methyl, nitrosyl, sulphonyl and amino phthalocyanines; azo dyes such as those listed in C H Munro et al, *Analyst* (1995), 120, p993; azomethines; cyanines and xanthines such as the methyl, nitro, sulphano and amino derivatives; and succinylfluoresceins. Each of these may be substituted in any conventional manner, giving rise to a large number of useful labels.

The choice of label in any given case will depend on factors such as the resonance frequency of the label, the other species present, label availability, choice or laser excitation equipment etc. In particular it may be selected such as to maximally distinguish between SAS associated with the metal surface which is not capable of surface enhancement, and that associated with the metal surface which is capable of surface enhancement (i.e. part of a target sequence/TBS complex.

It may be preferred that the SAS is an azo group, which can be very easily derivatised. The skilled person will appreciate, however, that other SAS may also be readily employed in the invention.

The dye may be associated with the metal surface using either covalent or non-covalent interactions. Particular preferred is the use of SSGs as described above SER(R)S detection This can be by conventional methods, for instance as disclosed in WO 97/05280 (University of Strathclyde).

Thus in SE(R)RS the primary measurements are of the intensity of the scattered light and the wavelengths of the emissions. Neither the angle of the incident beam nor the position of the detector is critical. With flat surfaces an incident laser beam is often positioned to strike the surface at an angle of 60° with detection at either 90° or 180° to the incident beam. With colloidal suspensions detection can be at any angle to the incident beam, 90° again often being employed.

Several devices are suitable for collecting SE(R)RS signals, including wavelength selective mirrors, holographic optical elements for scattered light detection and fibre-optic waveguides. The intensity of a SE(R)RS signal can be measured using a charge coupled device (CCD), a silicon photodiode, or photomultiplier tubes arranged either singly or in series for cascade amplification of the signal. Photon counting electronics can be used for sensitive detection. The choice of detector will largely depend on the sensitivity of detection required to carry out a particular assay.

For multiple, different analytes, a complex SE(R)RS spectrum across a range of wavelengths will be obtained. Although analysis by eye may be possible, methods for obtaining and/or analysing a SE(R)RS spectrum will preferably include the use of some form of data processor such as a computer.

Note that the methods of the invention may involve either obtaining a full SE(R)RS spectrum across a range of wavelengths, or selecting a peak and scanning only at the wavelength of that peak (i.e., Raman "imaging").

Preferably the excitation beam is selected to maximally distinguish between the SAS associated with the metal surface which is not capable of surface enhancement, and that associated with the metal surface which is (i.e. part of a target sequence/TBS complex.

For instance if the plasmon resonance of the metal surface (following aggregation) is 600 nm, and the SAS is also active in this region, then the excitation beam will be selected to be in this region to maximise surface enhancement and resonance effects. When using multiple, differing, SAS groups, excitation frequency may be chosen to closely match the absorbance maxima of the SAS in order to provide sharp signals thereby improving the molecular specificity of detection.

Preferred formats

Certain preferred formats are discussed below. Naturally the skilled person will appreciate that these are not obligatory, and that other methods which also achieve the advantages of the present invention, and are based on the disclosure herein, may be equally be used if preferred.

Arrangements of SER(R)S dye, TBS, and metal surface.

Some of these are illustrated in FIG. 3.

Two agents comprising different TBS may be used—each TBS may be attached to the metal surface (for instance of prepared monodisperse, unaggregated colloids) via a linker and an SSG (e.g. based on benzotriazole) incorporating an SAS (e.g. an azo group). The components of the agents are prepared together in situ or are pre-mixed, and then added to the sample. Raman imaging or spectroscopy is then carried out as desired.

Alternatively, for each of the two agents, separate TBS and SAS, each incorporating an SSG, may be pre-mixed in the desired proportions, and the mixture applied to metal colloid to coat it. The two agents are then added to the sample, and the observation for surface enhancement is made.

The preferred ratio TBS:SAS may be greater or less than 1:1. However, preferably the SAS is present in excess over the TBS, for instance greater than 10, 20, 30, 40, or 50 fold excess. The preferred ratio of TBS-SSG: SAS-SSG is about 1:100. As discussed above, generally speaking, sensitivity will be improved by maximising the number of molecules of SAS which are surface-enhanced by a single binding event (i.e. two TBS molecules to one molecule of target sequence). This is achieved by maximising the number of molecules of SAS which are present on the metal colloid particles brought together by the binding event. However care must be taken (e.g. for reasons of economy) to ensure that at least some TBS-SSG, preferably evenly distributed, is present on each metal/SAS complex, in order to give it functionality.

Multiplexing

Raman signals consist of a series of discrete spectral lines of varying intensity. The frequencies and the relative intensities of the lines are specific to the label being detected and the Raman signal is therefore a "fingerprint" of the SAS.

If the analyzer is being used to quantitate the detection of one (e.g. as described above) label then it will only be necessary to detect signal intensity at a chosen spectral line frequency.

However more than one detection agent may be used simultaneously to probe for more than one target sequence by using detection agents having distinctive, distinguishable, SAS.

If the analyzer is being used to quantitate the detection of several labels, each of which has a unique spectral line, then it will only be necessary to detect signal intensity at several chosen spectral line frequencies. Otherwise, if a SE(R)RS analyzer is being used selectively to detect one or more 'bound' agents out of a mixture, it will be necessary to detect the entire "fingerprint" spectrum for identification purposes.

In cases where the target sequences share some sequence identity (e.g. distinguishing target sequences containing single nucleotide polymorphisms), a common first agent may be used, provided that the second agent can in each case discriminate between the remainder of the target sequence, and can itself be distinguished from the other second agents by use of a distinctive SAS.

Alternatively, for detecting several quite distinct sequences, several pairs of agents may be used, provided only that they are not self-complementary.

Further aspects of the invention

As discussed in the Introduction, the methods may have numerous applications in genomics, whereby they can be used analogously to existing methods which employ a step of in which nucleic acid sequence is analysed (see e.g. "Principles of Genome Analysis" by S B Primrose, Pub. Blackwell Science, Oxford, UK, 1995).

Some specific applications are as follows. Generally speaking all of these can be carried out using the single target sequence, or multiplexing approach. In the latter case, the combination of various results may be used to make a determination:

(i) Detection of the presence of an organism (e.g. virus, provirus, virion, prokaryote (such as bacterium), eucaryote (such as protozoan)) in a sample wherein the presence of the target sequence is associated with the presence of the organism, for instance because the sequence is unique to that organism.

Even in cases where the sequence probed may not actually be unique to the organism, its presence (in conjunction with other diagnostic information e.g. immunological, behavioural etc.) may be used to increase the certainty of a determination of its presence of absence. The detection may be confirmed where still further certainty is required by full sequencing.

The sample in this case can be anything suspected of containing the organism e.g. a sample taken from a different organism, a foodstuff, an environmental sample (e.g. soil, water etc.) The organism may be pathogenic, or may simply be associated with some other quality of interest.

(ii) Diagnosis of a disease associated with a pathogenic organism, by carrying out a determination as described above. The sample may be in vitro or in vivo. The test may be carried out in conjunction with other diagnostic techniques, or an assessment of symptoms etc.

(iii) Diagnosis of a disease associated with a DNA variation, by detecting the presence of the DNA variant comprising use of a method as discussed above wherein the target sequence corresponds to the sequence in which the variation occurs. The test may be carried out in conjunction with other diagnostic techniques, or an assessment of symptoms etc.

(iv) A method of selecting an organism having a particular phenotypic trait whereby the target sequence corresponds to a sequence associated with that trait.

(v) A method of isolating a nucleic acid encoding a specific gene whereby the target sequence corresponds to a sequence associated with, or within, that gene.

(vi) A method of phylogenetic classification, wherein the target sequence is associated with a particular individual, population, species, genus etc.

(vii) A method of identifying an individual wherein the target sequence is associated with that individual. Generally speaking this may entail scoring a number of discrete polymorphisms (see e.g. WO 96/01687 of Tully et al for sequences used in forensic typing and matching).

(viii) A method of expression profiling a cell or tissue. In this case the sample nucleic acid is mRNA, or is derived from it (e.g. cDNA).

In a further aspect of the invention there is disclosed a method of producing a detection agent comprising: combining unaggregated metal particles with a SER(R)S active species (SAS) and a target binding species (TBS), whereby said SAS and TBS combine with said metal particles via a surface seeking group.

In a further aspect of the invention there is disclosed a detection agent comprising: an unaggregated metal particle, being associated with a SER(R)S active species (SAS) and with a target binding species (TBS).

The various components of the agent may be any of those discussed above. In particular the SAS and the TBS are preferably bound to metal particle via an SSG, optionally in the form of a single molecule. Preferably the TBS and SSG are discrete molecules. Preferably the TBS is PNA or propargyl amino modified DNA. Preferably the SAS is an azo group and the SSG is benzotriazole.

In one embodiment the agent comprises a first agent and a second agent each having a different TBS.

In a further aspect there is disclosed a composition comprising two or more detection agents as described above, each having a distinctive SAS.

The agents or compositions of the present invention will generally be provided as solutions.

In a further aspect there is disclosed a kit comprising the agents or compositions of the present invention, plus one or more additional materials for practising the methods of the present invention e.g. target nucleic acid for control experiments.

In a further aspect there is disclosed a system comprising an agent or composition described above plus a nucleic acid sample, which is preferably a sample of DNA or RNA, most preferably extracted from a cell taken from or constituting an organism.

Such a system may particularly comprise:
(i) a reaction vessel,
(ii) an agent as described above,
(iii) a nucleic acid.
preferably in a homogenous format.

In a further aspect there is disclosed an apparatus comprising a SERRS analyser plus an agent, composition or system as described above, and methods of use of such an apparatus, comprising (for instance) the steps of preparing and monitoring (e.g. at between 500 and 600 nm) a homogenous system in order to detect a SER(R)S signal.

The invention will now be further explained with reference to the following non-limiting Figures and Examples. Other embodiments falling within the scope of the present invention will occur to those skilled in the art in the light of these.

FIGURES

FIG. 1: this shows the visible absorption spectra for a citrate colloid aggregated with (a) nitric acid, and (b) poly (L-lysine) and ascorbic acid. The dotted line represents the spectrum of unaggregated, monodisperse, citrate silver colloid prior to aggregation.

FIG. 2: this shows Formulae A1–A13 representing various SSGs which may be employed in the present invention.

FIG. 3: this shows various different formats for performing the present invention.

In (a)(i) an agent, which itself comprises two types of silver colloid particle is used. Each particle carries a different PNA probe (the TBS) which are designated X and Y respectively. These are associated with the metal surface via different dyes (the SAS) designated A and B, which interact with the metal surface via linkers and surface seeking groups (not shown). When combined with appropriate genomic material having a target sequence X'-Y' (containing portions complementary to X and Y) the silver colloid particles are aggregated, this aggregation can be monitored via one or both of dyes A and B (one of which could be omitted if not required).

In (b) an alternative agent is shown. In this case the dye (A) and PNA probe (X) are separately associated with the metal surface, each via a linker and surface seeking group (not shown).

In (c) a method for distinguishing and scoring polymorphisms is shown. In this case the possible target sequences are X'-Y' and X'-Y2'. These can be distinguished by using an additional colloid particle type, having an appropriate PNA probe (designated Y2) and a dye which is distinguishable from B (designated C). By observing which of B and C is surface enhanced, the target sequence can be elucidated. It may be desirable to label common sequence colloid particle (X) with dye A as a control, since this should be detectable for either polymorphism.

In (d) a method for probing discrete sites is shown. This is similar to (c) but there is no common sequence between the target sequences, therefore four different types of colloid particle are used. The detection of dye D indicates the presence of target sequence V'-W'.

Figure 4:
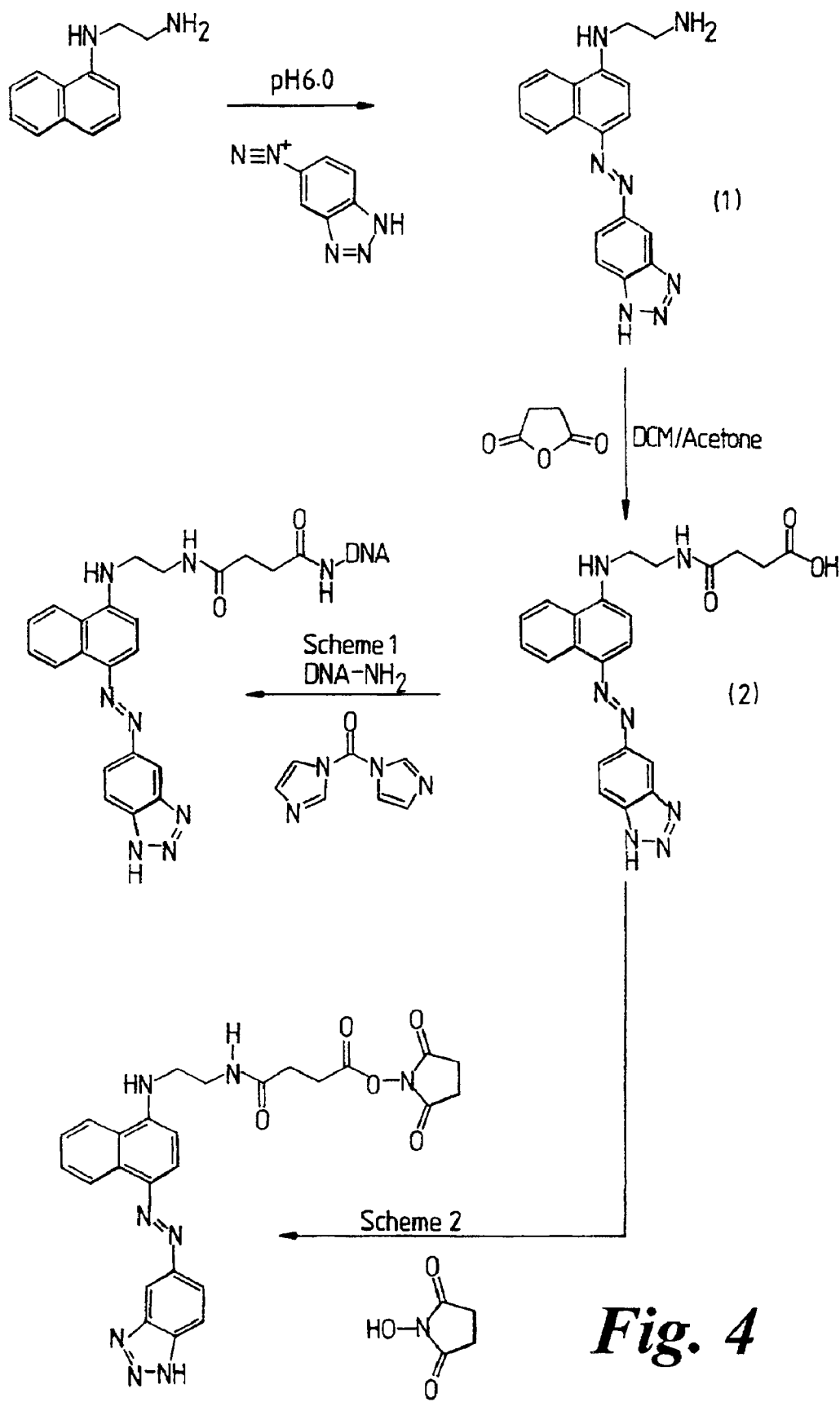

FIG. 4: this shows a pathway for producing an amino derivative of benzotriazole dye [$N^1$-[4-(5-Azobenzotriazoyl)phenyl]-ethane-1,2-diamine—Compound (1)], and a carboxylic acid derivative of this [$N^1$-[4-(5-Azobenzotriazoyl)phenyl amino-ethyl]-succinamic acid—Compound(2)]. The carboxylic acid derivative may be attached to DNA (Scheme 1) or used to produce an active ester (Scheme 2) for subsequent attachment.

Figure 5:
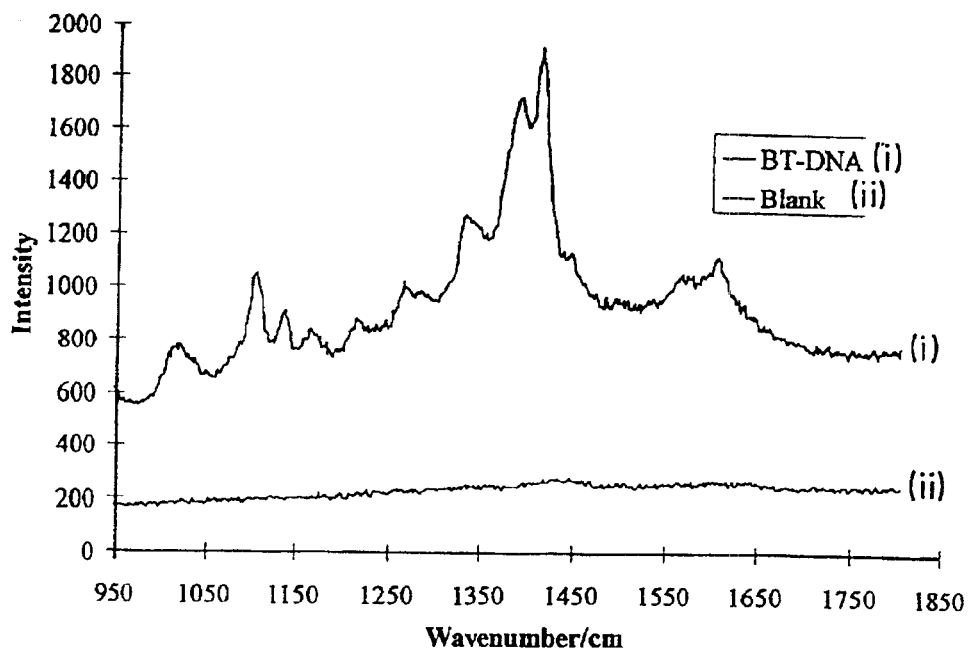

FIG. 5: this shows a SERRS spectrum of a benzotriazole dye labelled 26mer DNA oligonucleotide.

Figure 6:
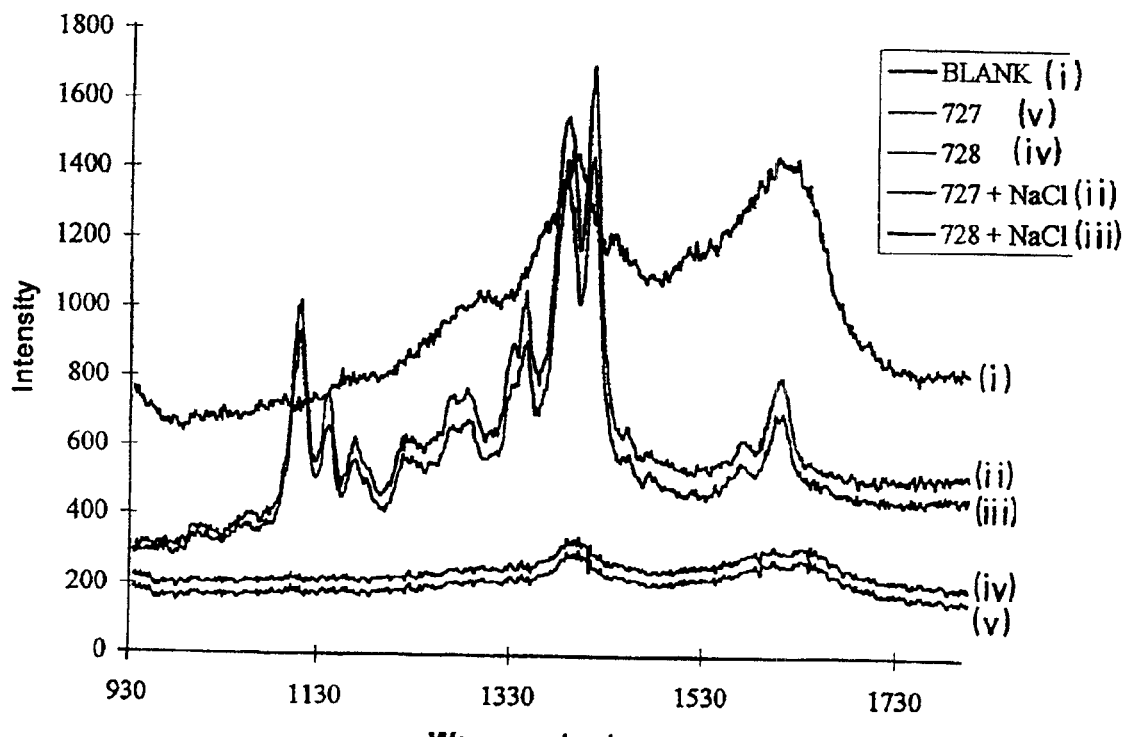

FIG. 6: this shows a SERRS spectrum of benzotriazole dye labelled PNA oligonucleotides in presence and absence of aggregating agent.

Figure 7:
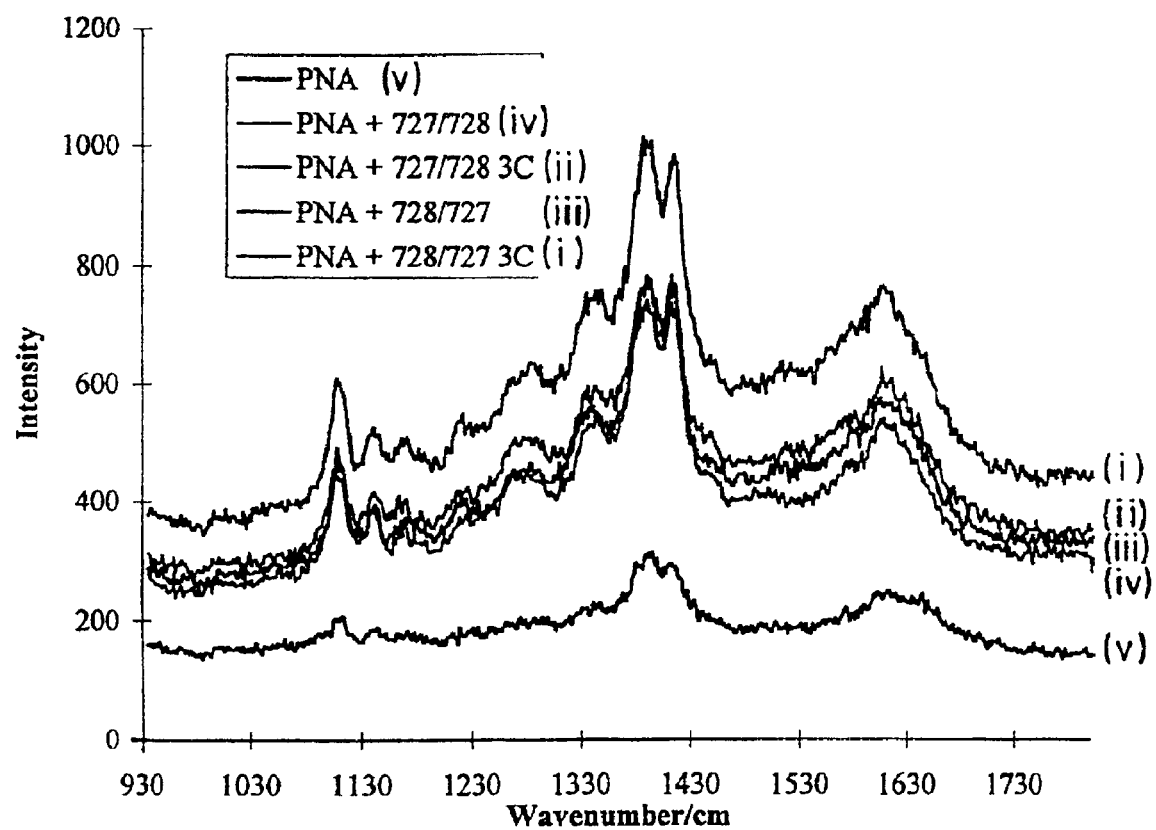

FIG. 7: this shows a SERRS spectrum of benzotriazole dye labelled PNA oligonucleotides in presence and absence of complementary target sequences.

EXAMPLES

Example 1

Overview of Synthesis of Labelled PNA Probes and Subsequent Use

Basic synthesis involves the addition of a carboxylic acid or an active ester form of a benzotriazole dye to the amino terminus of a PNA probe, optionally while the PNA is on a solid support used for synthesising it. The probe consists of eight or more bases complementary to part of a target sequence found in genomic DNA. Thus the bases will still be protected, but the primary amine is free for reaction.

a) Synthesis of Benzotriazole Carboxylic Acid or Active Ester

An amino alkylated aromatic amine, such as N-(1-naphthyl)ethylenediamine dihydrochloride, is coupled to aminobenzotriazole via a diazonium coupling to produce a monoazo dye. The free amine then reacts with succinic anhydride to provide a carboxylic acid (see FIG. 4).

In more detail, to provide $N^1$-[4-(5-Azobenzotriazoyl)phenyl]-ethane-1,2-diamine (=Compound 1), 5-Aminobenzotriazole (0.854 g, 1.1 eq, 6.37 mmol), was dissolved in HCl (5ml, 50% v/v) and diazotised by dropwise addition of sodium nitrite (0.484 g, 1.2 eq, in 5 ml $H_2O$) at 0° C. An excess of sodium nitrite was detected using starch iodide paper. A dark blue colour indicated excess nitrous acid which inferred the formation of the diazonium salt. Separately N-(1-Naphthyl) ethylenediamine dihydrochloride (1.500 g, 5.79 mmol) was dissolved in sodium acetate buffer (1.0M, 60 ml, pH 6.0) and acetone (80 ml). Diazotised aminobenzotriazole (1.1 eq) was added to this solution dropwise at 0° C. with stirring over 1 hour after which the solution was neutralised by addition of sodium hydroxide (2M). The solid produced was isolated by filtration and washed with sat. KCl (3×50 ml) prior to purification by trituration using methanol and diethyl ether to produce the title compound as an orange solid in 66% yield Rf (EtOAc/$CH_3OH/NH_3$ 5/1/1) 0.14; $d_H$ (270 MHz, $CD_3OH$) 3.00 (2H, t, $CH_2$) 3.48 (2H, t, $CH_2$) 6.69 (1H, dd, arH) 7.51 (1H, t, arH) 7.63 (1H, t, arH) 7.87 (1H, d, arH) 7.94 (2H, m, arHs) 8.13 (1H, d, arH) 8.34 (1H, s, arH) 9.02 (1H, d, arH); $d_c$(270 MHz, $CD_3OD$) 41.40 ($CH_2$) 47.01 ($CH_2$) 104.26 (CH) 114.93 (CH) 115.13 (CH) 116.67 (CH) 117.47 (CH) 122.20 (CH) 124.26 (C) 124.73 (CH) 126.03 (CH) 127.91 (CH) 134.62 (C) 139.91 (C) 146.12 (C) 146.76 (C) 148.98 (C) 151 28 (C); FAB ms m/z 332.1621 [$C_{18}H_{18}N_7$ (M+1) <0.1 ppm].

In order to provide $N^1$-[4-(5-Azobenzotriazoyl)phenyl amino-ethyl]-succinamic acid (=Compound 2), Compound (1) (1.000 g, 3.02 mmol) was dissolved in DMF (100 ml) and left to stir. Succinic anhydride (0.363 g, 1.2 eq, 3.63 mmol) dissolved in acetone (10 ml) was then added dropwise over one hour. After 18 hours the solvent was removed in vacuo and the product isolated by column chromatography (pre-absorbed onto $Na_2SO_4$) eluting with ethyl acetate, methanol and ammonia (5/1/1) to produce an orange solid which was further purified by trituration from diethyl ether to give 0.856 g (66% yield) of the pure product Rf (ethyl acetate/methanol/ammonia 5/1/1) 0.11; $d_H$ (400 MHz, DMSO-d6) 2.40 (2H, dd, $CH_2$) 2.44 (2H, dd, $CH_2$) 3.42 (4H, m, 2×$CH_2$) 6.66 (1H, brs, NH) 6.76 (1H, d, arH) 7.32 (1H, m, arH) 7.54 (1H, t, arH) 7.67 (1H, t, arH) 7.90 (1H, d arH) 7.99 (1H, dd, arH) 8.25 (1H, d, arH) 8.29 (1H, s, arH) 8.98 (1H, d, arH).

If an active ester is desired then the succinyl form can be produced from the carboxylic acid by activating with hydroxy succinimide as shown in FIG. 4—scheme 2).

It should be stressed that any length or nature of linker may be used.

b) Addition of surface-seeking group to nucleic acid

The carboxylic acid form of the benzotriazole dye is coupled to the solid supported nucleic acid by standard methods commonly used for such couplings. Deprotection and removal from the solid support followed by purification yields the desired product.

In more detail, for coupling Compound (2) to DNA, the desired DNA sequence was synthesised according to standard solid phase phosphoramidite chemistry using Expedite fast deprotection monomers on a 0.2 mmol scale. An amino linker (standard monomethoxytrityl aminohexyl phosphoramidite) was added to the 5'-terminus of the oligonucleotide and deprotected on column to leave a free amine for reaction. The column was then removed from the synthesiser and a manual coupling of compound (2) per-formed. Compound (2) (54.7 mg, 0.12 mmol) was dissolved in DMF (2 ml) and N,N-carbonyldiimidazole (30.4 mg, 1.56 eq, 0.187 mmol) added. The mixture was stirred at 40° C. for five minutes before cooling to room temperature and passed through the oligonucleotide synthesis column via two syringes in a standard method. The solution was allowed to react for 2 hours before being removed and ammonia (1 ml) added to facilitate cleavage and deprotection. After 2 hours the ammonia was removed and the residue purified by anion ion exchange HPLC.

The purified sample was then passed through a sephadex G25 column for desalting prior to freeze drying. Dissolution in water afforded a 30.5 mM solution.

The above procedure was also used to add benzotriazole carboxylic acid to the 5'-terminus of the 26mer target oligonucleotide to produce a 55.4 mM solution.

In order to add Compound (2) to PNA, a solution of compound (2) (0.18 M) was added to port 6 of the synthesiser and a special coupling step for this port inserted into the standard PNA cycle. The step extended the coupling time for the novel base to 30 minutes from 15 minutes. The desired 8mer sequence was synthesised by standard PNA chemistry on a 2 mmol scale. An amino linker was then added to the N-terminus followed by the modified benzotriazole dye using the modified cycle. Deprotection by trifluoroacetic acid followed by purification by reverse phase HPLC and subsequent freeze drying yielded the desired compounds. The following solutions were obtained by dissolving the lyophilised solids in water:

```
727    (N—C) 6O ACA TTT GA    12.08 mM
728    (N—C) 6O ACA TGG TC    18.20 mM
``` where:
 $6=N^1$-[4-(5-Azobenzotriazoyl)phenyl amino-ethyl] succinamic acid (=Compound 2)
 O=amino linker c) Attachment to the Colloid An aqueous solution of the labelled e.g. PNA probe is mixed with a suitable amount of colloid. The amount of probe used is just less than the amount required for monolayer coverage of the colloidal particles present.

Example 2

Carrying Out Detection (a) Labelled DNA

A SERRS spectrum of the benzotriazole dye labelled 26mer DNA oligonucleotide has been obtained and is shown in FIG. 5.

The SERRS signals were only visible once an aggregating agent (spermine) had been added thus confirming that benzotriazole dye labelled DNA could be added to colloid without producing any signals and that a hybridisation-linked aggregation could generate a detectable change.

(b) Labelled PNA

As described above, the two non-complementary sequences of PNA are attached, via an N-terminus-SERRS label, to separate colloidal silver particles using is monoazobenzotriazole compounds to provide effectively irreversible attachment of the PNA to the surface. This provides a system which will consecutively hybridise to a complementary sequence on a parent strand.

When the two colloidal mixtures containing the tethered specific nucleic acid or nucleic acid analogue sequences are mixed together then irradiated, no SERRS signal is observed owing to the non-aggregated nature of the metal surface.

An aqueous solution of the test sequence is added to the above mixture of PNA labelled colloid and after a suitable period of time for hybridisation and hence aggregation, irradiation yields the signals corresponding to the two labels which are detected on conventional SER(R)S equipment. Aggregation only occurs in the presence of the correct complementary sequence. Therefore if a signal is observed the presence of the sequence under scrutiny will be confirmed (see FIG. 3(a)).

Owing to the sensitivity of the process no amplification of the target DNA is required. Also the time scale from taking a sample, isolating the desired target nucleic acid then conducting the assay will be greatly reduced compared to many methods currently employed.

In one experiment, labelled PNA sequences as detailed in Example 2 were examined for SERRS activity.

Initially an estimated surface coverage of 600 molecules per colloidal particle was examined. In these experiments it was found that both labelled 727 and labelled 728 sequences gave extremely intense and distinctive spectra at this level without the use of any external aggregating agent (spectra obtained using $3 \times 10^{-11}$ moles for one second at 514.9 nm, results not shown). This finding was believed to arise from the use of trifluoroacetic acid to help dissolve the final purified PNA which may have aggregated the colloid thus providing signals.

In order to address this effect, another concentration level was attempted. The level attempted was roughly equivalent to 12 PNA oligomers per colloidal particle which meant the use of $6 \times 10^{-13}$ moles. The spectra were accumulated for 5 seconds and did not produce any signals in absence of an aggregating agent. To prove signals could be produced 20 μl of 5% sodium chloride solution (a well known colloidal aggregating agent) was added. Distinctive signals were produced thus indicating that at this level SERRS could be obtained by aggregation. The spectrum is shown FIG. 6.

In order to show a hybridisation-linked effect, two different labelled PNA oligomers were first mixed to determine whether a signal is produced. FIG. 7 (PNA) shows that when this happens some weak signals can be seen over 5 seconds. This mixture was then subjected to four different complementary oligonucleotides to see if aggregation would occur.

The oligos used were: (20 ml of $1 \times 10^{-6}$ M solution for each to provide an excess)

```
TCA AAT GTG ACC ATG T        727/728 complement
TCA AAT GTC CCG ACC ATG T    727/728 3C complement
GAC CAT GTT CAA ATG T        728/727 complement
GAC CAT GTC CCT CAA ATG T    728/727 3C complement
```

The spectra after 30 minutes are shown below in FIG. 7. Accumulation time=5 seconds.

The above spectra show that aggregation occurs when the oligonucleotides are added, although the signal intensity is about half that observed when sodium chloride is used, possibly implying inefficient aggregation or hybridisation, which may in turn be due to the level trifluoracetic acid used in the Example. Notwithstanding this results clearly show that the binding of a TBS to a target sequence can be used to increase the level of surface enhancement of a SAS present in the system.

Example 3

Using Separate SAS and TBS

There is no requirement that the SAS (e.g. dye) and TBS (e.g. PNA) be incorporated into a single molecule. They can be separately associated with the metal surface.

For instance, benzotriazole may be associated with the N-terminus of PNA or 5'-terminus of DNA (the latter optionally via an amino linker, while attached to controlled pore glass by analogy with standard extension techniques). A separate SAS dye group may be conjugated to benzotriazole (e.g. to form an azobenzotriazole group).

Figure 3A:
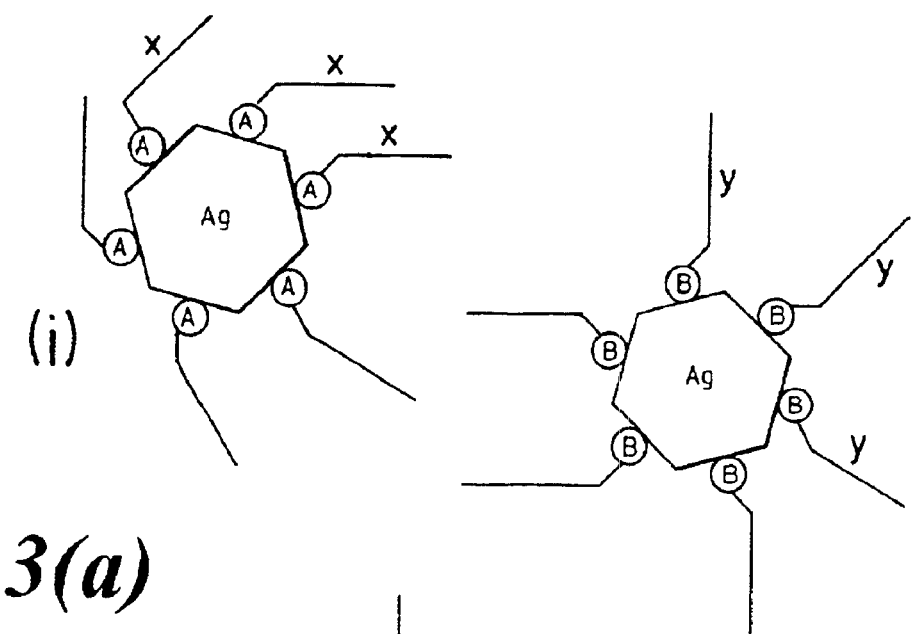
Figure 3B:
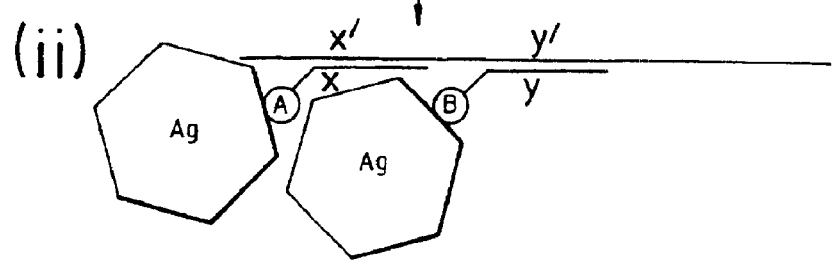
Figure 3B:
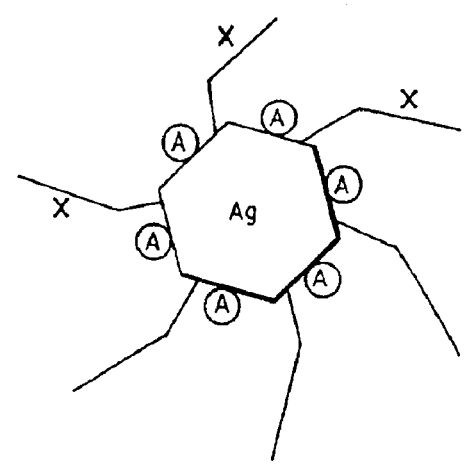
Figure 3C:
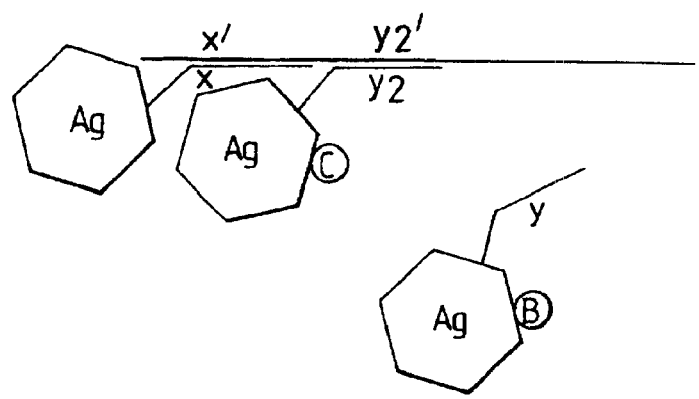
Figure 3D:
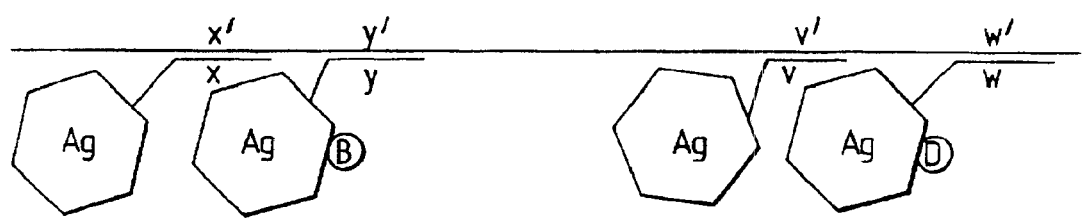

Generally speaking an excess of dye to PNA will be required (see FIG. 3(b)). Assuming a colloidal particle approximates to a sphere of radius 20 nm, this has a surface area of approx. $1 \times 10^{-15}$ m$^2$.

Using benzotriazole as a SSG (for both the dye and PNA), the size of this molecule can be taken as a square $10 \times 10^{-10}$ m by $10 \times 10^{-10}$ m. This gives an area per molecule of $1 \times 10^{-18}$ m$^2$. Therefore the number of molecules required for monolayer coverage is approx. 1200.

If it is desired to form cross linked aggregated, then (assuming face centred cubic packing) each particle may theoretically be surrounded by 12 others. This means that due to the size of the PNA compared to the colloid only the PNA attached near to an adjacent particle will be effective in providing aggregation. Hence a ratio of 100 dye molecules to one PNA may be desirable.

Example 4

Polymorphisms and Multiplexing

By tagging specific sequences (or metal surfaces associated therewith) with specific labels, a range of sequence permutations can be examined in one experiment. Thus it is possible to probe long strands and even whole genes of denatured DNA for specific sequences (see FIGS. 3(c) and 3(d)).

Example 5

Detailed Assay for Polymorphism

Choice of pre-prepared labelled colloidal suspensions for desired assay (5 mins)

The colloidal batches may contain up to five different labelled sequences. One for the strand away from the mutation and four for each of the possible mutations. In circumstances where it is believed that there are fewer than four possible base identities, or where it is not desired to score the polymorphism, but only confirm that it is not a given base, fewer labelled sequences may be used.

Preparation of assay (2 mins)

An aliquot (10 µl) from each of the desired labelled colloids is mixed together in an ependorf. A small portion of this mixture (20 µl) is kept aside as a control.

Preparation of sample nucleic acid (30 mins)

The nucleic acid sample to be analysed is isolated from the original sample (e.g. a blood sample) by conventional methods (see e.g. *Molecular Cloning: a Laboratory Manual:* 2nd edition, Sambrook et al, 1989, Cold Spring Harbor Laboratory Press, or later editions of that work) and desalted prior to dissolution is water (20 µl)

Detection of sequence or point mutations (5 mins)

The sample nucleic acid is added to the mixture of colloids and the correct strands allowed to hybridise. After hybridisation the suspension is transferred to a capillary tube (d=1 mm, length=5 mm) for detection by SERRS.

Alternatively the various components of the assay could be prepared and carried out in a single vessel which is also used for the spectroscopy, to provide a simpler, homogenous protocol.

Analysis of signals obtained (5 mins)

Computer comparison of the signals obtained with those stored for the individual labels allows accurate identification of the colloid used and hence the sequence or point mutation present in the sample. Quantitation of the amount of material present and the frequency of a certain sequence or point mutation may also be carried out. The detection limits may be estimated as follows:. published work shows that labels are detectable at a concentrations of $8 \times 10^{-13}$ M (or even lower). For detection in a cylinder of volume 4 µl, this equates to 2000000 molecules. Since there may be 100 or more dye molecules per TBS, this equates to a target level of only 20000 molecules ($3 \times 10^{-20}$ moles). The sensitivty may be even higher for particular dyes.

REFERENCES (1) Graham, D.; MacLaughlin, C.; McAnally, G.; Smith, W. E.; Jones, J.; White, P. C. *Chemical Communications* (1998) 11, 1187–1188.
(2) Mirkin, C. A.; Letsinger, R. L.; Mucic, R. C.; Storhoff, J. J. *Nature* (1996) 382, 607–609.
(3) Alivisatos, A. P.; Johnsson, K. P.; Peng, X.; Wilson, T. E.; Loweth, C. J.; Bruchez, M. P.; Schultz, P. G. *Nature* (1996) 382, 609–611.
(4) Munro, C. H.; Smith, W. E.; White, P. C. *Analyst* (1995) 120, 993–1003.
(5) Graham, D.; Smith, W. E.; Linacre, A. M. T.; Munro, C. H.; Watson, N. D.; White, P. C. *Analytical Chemistry* (1997) 69, 22, 4703–4707.

What is claimed is:

1. A method for determining the presence or absence of a target nucleic acid sequence in a sample nucleic acid, the method comprising:
   (a) exposing the sample to a detection agent comprising at least two separate components, including a first agent having a metal surface associated with a first target binding species (TBS) and a second agent having a metal surface associated with a second TBS, different from said first TBS, at least one of said metal surfaces being associated with a SER(R)S-active species (SAS), each of said first and second TBS being effective to bind to the target sequence, and wherein the binding of the first and second TBS to the target sequence causes aggregation of the metal surfaces associated with said TBS, thereby causing surface enhancement of a SAS associated with one or both of the metal surfaces, said metal surfaces being ineffective to cause surface enhancement in the form in which they are present in the detection agent to which said sample is exposed, and aggregation of said metal SER(R)S surface being dependent on the presence of said target nucleic acid in said sample; and,
   (b) observing the sample/agent mixture using SER(R)S to detect any said surface enhancement.

2. The method as claimed in claim 1 wherein each component of said detection agent comprises monodisperse unaggregated colloidal metal particles associated with a TBS comprising a nucleic acid or nucleic acid analog which is complementary to all or part of the target sequence.

3. The method as claimed in claim 2 wherein the TBS comprises propargyl amino modified nucleic acid or peptide nucleic acid.

4. The method as claimed in claim 2 wherein there are up to 20 TBS per metal colloid particle.

5. The method as claimed in claim 1 wherein a surface seeking group (SSG) is used to promote chemisorption of at least one of the SAS and TBS to the metal surface.

6. The method as claimed in claim 5 wherein the SSG comprises a triazole group.

7. The method as claimed in claim 5 wherein the SSG is modified with a dye which is a SAS.

8. The method as claimed in claim 7 wherein the modified SSG is an azobenzotriazole.

9. The method as claimed in claim 7 wherein the modified SSG is used to associate the TBS to the metal surface.

10. The method as claimed in claim 9 wherein the modified SSG is conjugated to the TBS via a linker group.

11. The method as claimed in claim 1 wherein the SAS is present in an amount of up to 100 fold excess over the TBS.

12. A method as claimed in claim 1 wherein more than one target sequence is determined using detection agent components having distinguishable SAS.

13. A method as claimed in claim 12 wherein the target sequences share sequence identity, and wherein a common first agent is used in conjunction with specific distinguishable second agents which can discriminate between the remainder of the target sequences.

14. A method for detecting the presence of, or selecting, or identifying, or phylogenetically classifying, an organism,, the method comprising use of a method as claimed in claim 1 wherein the target nucleic acid sequence is associated with that organism.

15. A method for diagnosing a disease, the method comprising use of a method as claimed in claim 1 wherein the target nucleic acid sequence is associated with that disease.

16. A method for isolating a nucleic acid encoding a specific gene, the method comprising use of a method as claimed in claim 1 wherein the target sequence corresponds to a sequence associated with, or within, that gene.

17. The method as claimed in claim 6 wherein said triazole group is the benzotriazole group.

* * * * *